United States Patent [19]

Schmid et al.

[11] 4,212,817
[45] Jul. 15, 1980

[54] CONTROL OF HIGHLY EXOTHERMIC CHEMICAL REACTIONS

[75] Inventors: Herbert Schmid, Wolfratshausen; Helmut Schneider, Grunwalt; Allan Watson, Ottobrunn, all of Fed. Rep. of Germany

[73] Assignee: Linde Aktiengesellschaft, Wiesbaden, Fed. Rep. of Germany

[21] Appl. No.: 588,515

[22] Filed: Jun. 19, 1975

[30] Foreign Application Priority Data

Jun. 26, 1974 [DE]  Fed. Rep. of Germany ....... 2430769

[51] Int. Cl.$^2$ ............................................... C07C 1/04
[52] U.S. Cl. ..................... 260/449 M; 260/449.6 M; 423/659; 423/DIG. 6; 165/1; 165/11 R; 165/13; 165/26; 422/198
[58] Field of Search .................. 260/449 M, 449.6 M; 423/659 G, DIG. 6; 165/1, 11, 13, 26

[56] References Cited

U.S. PATENT DOCUMENTS

| | | | |
|---|---|---|---|
| 2,662,911 | 12/1953 | Dorschner et al. | 260/449.5 X |
| 3,441,393 | 4/1969 | Finneran et al. | 260/449 M X |
| 3,642,460 | 2/1972 | Thompson | 260/449 M |
| 3,854,895 | 12/1974 | Muller | 260/449 M X |
| 3,890,113 | 6/1975 | Child et al. | 260/449 M |
| 3,904,386 | 9/1975 | Graboski et al. | 260/449 M X |
| 3,927,998 | 12/1975 | Child et al. | 260/449 M X |
| 3,927,999 | 12/1975 | Child et al. | 260/449 M |
| 3,958,956 | 5/1976 | Goeke | 260/449 M |

FOREIGN PATENT DOCUMENTS

| | | | |
|---|---|---|---|
| 1110147 | 7/1961 | Fed. Rep. of Germany | 260/449.6 M |
| 791946 | 3/1958 | United Kingdom | 260/449 M |

OTHER PUBLICATIONS

Hougen et al., Chemical Process Principles, Kinetics & Catalysis, J. Wiley, New York, Part 3, 1947, pp. 1031-1033.

*Primary Examiner*—Howard T. Mars
*Attorney, Agent, or Firm*—Millen & White

[57] ABSTRACT

Highly exothermic continuous chemical reactions such as the methanization of carbon oxides are cooled by indirect heat exchange with a liquid coolant such as water, thereby converting at least some of the liquid to a vapor such as steam. When the reaction temperature, because of operational difficulties or the like, exceeds the design temperature of the reaction, said vapor such as steam is passed into the reaction chamber. In this way, the reaction stream is cooled as well as diluted; in addition, since the vapor is preferably selected to be a reaction product, the extent and rate of the exothermic reaction are diminished.

10 Claims, 1 Drawing Figure

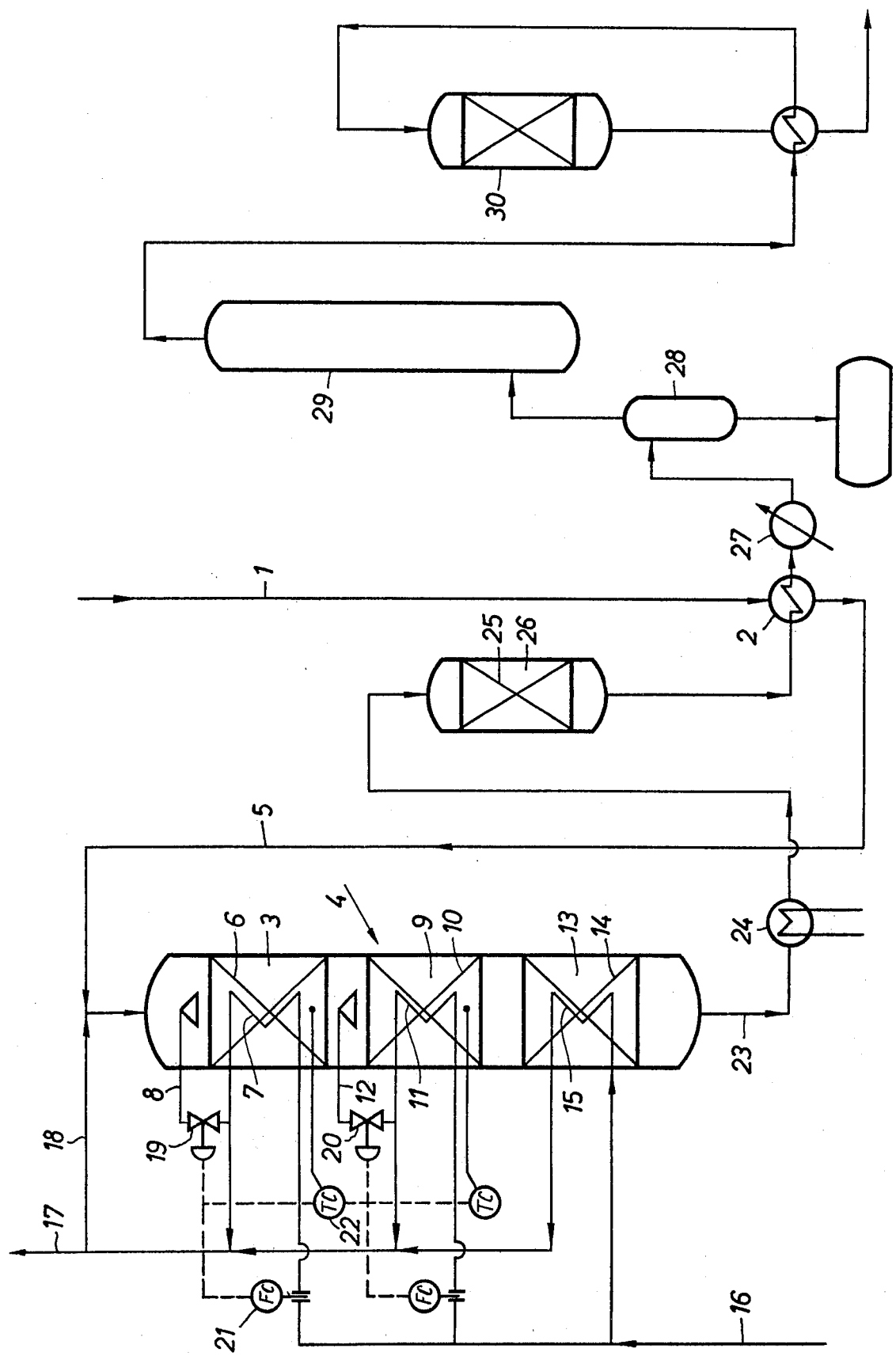

CONTROL OF HIGHLY EXOTHERMIC CHEMICAL REACTIONS

BACKGROUND OF THE INVENTION

This invention relates to a process and an apparatus for conducting a strongly exothermic, catalytically accelerated chemical reaction, wherein at least part of the thus-produced heat of reaction is removed by indirect heat exchange with a liquid.

In the operation of highly exothermic chemical reactions, a critical technical problem resides in controlling the heat of reaction liberated by the reactions. Thus, it was found that, e.g., the heat of reaction Q liberated during the methanization of carbon oxides with hydrogen with the use of a suitable catalyst, i.e. in chemical reactions taking place according to the reaction equations:

$$CO + 3H_2 \rightleftharpoons CH_4 + H_2O + Q$$

and/or $$CO_2 + 4H_2 \rightleftharpoons CH_4 + 2H_2O + Q$$

becomes so high that considerable difficulties exist in process technology when conducting this reaction, especially if the carbon oxide concentration in the charge gas to be treated is relatively high.

To avoid these difficulties, specifically for controlling the heats of reaction liberated during these reactions, it has been known to dilute the charge gas to be treated initially by a suitable inert gas, such as nitrogen, for example. Due to this reduction in concentration of the reactants in the charge gas, it has been possible, on the one hand, to lower the increase in temperature caused by the chemical reaction, but, on the other hand, this mode of operation leads to disadvantagesly large and expensive apparatus. Additionally, after the reaction, the inert gas must be separated, which requires still additional investment and energy costs.

It is also conventional in conducting an exothermic chemical reaction, for example for the removal of methylacetylene and ellene from hydrocarbon mixtures by treatment with hydrogen under pressure in the presence of hydrogenation catalysts, to remove the heat of reaction in indirect heat exchange with water or with another coolant (DAS [German Published Application] No. 1,062,693). It has been found, however, that this process cannot be readily employed with highly exothermic chemical reaction for the removal of very large amounts of heat, especially at a high temperature level.

SUMMARY OF THE INVENTION

An object of this invention is to provide a simple system, favorable from an energy viewpoint, for controlling a highly exothermic chemical reaction.

Upon further study of the specification and appended claims, further objects and advantages of this invention will become apparent to those skilled in the art.

These objects are attained, in accordance with the invention, by conducting the reaction in indirect heat exchange with a liquid coolant so that at least a portion of the liquid is vaporized. At least a portion of the thus-vaporized liquid is introduced into the reaction chamber as soon as the temperature in the reaction stage exceeds the maximum design value.

It is thus possible, by means of this invention, to prevent an undesirably high temperature increase within the reaction stage where the exothermic chemical reaction is conducted. First, an amount of reaction heat corresponding to the heat of evaporation of the indirectly heated liquid coolant is constantly withdrawn from the reaction stage, and by balancing the amount of liquid to be vaporized to the expected heat of reaction, an approximately constant temperature level can be maintained, corresponding, for example, to design limits within the reaction stage. Second, the direct introduction of a portion of the vaporized liquid into the reaction stage according to the invention effects, in case of an intermittent sudden, unforeseeably great increase in the heat of reaction within the reaction stage (which can be due for example to a faulty operation, to fluctuations of the concentrations of reactants in the gaseous charge, or also to load fluctuations) a rapid and effective readjustment of the temperatures within the reaction stage to the design limits. This direct surge of a portion of the vaporized liquid into the reaction stage results in a cooling of the charge gas. Furthermore, an increased amount of throughput must now be warmed, thereby diluting the heat of reaction. Additionally, owing to the increased volume of the stream, the residence time of the gaseous charge in the reaction stage is necessarily shortened.

It is especially advantageous to utilize an evaporating liquid the chemical composition of which corresponds to the chemical composition of a reaction product obtained during the chemical reaction. In this case, due to the law of mass action, the feeding of the vapor into the reaction stage effects a shift in the chemical equilibrium unfavorable to the formation of reaction products; as a consequence, the development of the heat of reaction is diminished. Besides, from the standpoint of reaction kinetics, the addition of the vapor has an inhibiting effect on the reaction rate.

All of these considerations contribute toward the rapid and safe reduction of an undesirably high temperature rise within the reaction stage.

In addition to the advantage with respect to temperature control within a reaction stage, the process of this invention also has energy advantages, since it is possible to utilize, for producing the additional vapor, the heat of reaction, i.e. the energy generated within the system proper, rather than an external energy.

According to a further feature of the invention, the chemical reaction can be conducted in several series-connected reaction stages, wherein at least in the first reaction stage the catalyst mass is dimensioned so that the reaction velocity of the reactants is insufficient for establishing a chemical equilibrium in this reaction stage. Advantageously, the catalyst mass in the individual stages are metered to such an extent that the reactants are in chemical equilibrium only after passing through the last reaction stage. This distribution of the course of the reaction over several reaction stages leads to a further improvement in controllability and thus to an increase in safety with regard to the operation of a strongly exothermic chemical reaction.

The process of this invention is suitable for conducting any highly exothermic chemical reaction and is basically independent of the character of the individual reactants.

This process can be utilized, however, with special advantage for the methanization of a gaseous charge of compounds of carbon and oxygen, especially carbon monoxide, by chemical reaction with hydrogen. In this case, water is used as the liquid to be vaporized, since for example during the methanization of carbon monoxide, i.e. during the production of synthetic natural gas, water is obtained in addition to methane as the reaction product, in accordance with the chemical reaction equation:

$$CO + 3H_2 \rightleftharpoons CH_4 + H_2O + Q$$

In accordance with the present invention, it is possible, for example, in the methanization of carbon monoxide, to employ readily a gaseous charge containing more than 50 vol.-% of carbon monoxide, for example, having been obtained during the gasification of coal. Moreover, the charge gas need not necessarily have a stoichiometric hydrogen-carbon monoxide ratio corresponding to the above-mentioned reaction equation.

Apparatus for conducting the process of this invention is distinguished by an at least one-stage reactor with a catalyst mass and at least one pipe coil in the reactor stage, as well as by a conduit in communication with the outlet of the pipe coil and the internal space of the reactor stage.

BRIEF DESCRIPTION OF DRAWING

The attached FIGURE is a schematic illustration of the preferred embodiment of the invention.

DETAILED DESCRIPTION OF DRAWING

The FIGURE illustrates a scheme of a plant for the production of methane by chemical reaction between hydrogen and carbon oxides. The chemical reaction takes place according to the formulae $$CO + H_2O \rightleftharpoons CO_2 + H_2 + Q$$

$$CO + 3H_2 \rightleftharpoons CH_4 + H_2O$$

$$CO_2 + 4H_2 \rightleftharpoons CH_4 + 2H_2O + Q$$

wherein Q denotes the heats of reaction liberated during the reactions.

According to the FIGURE, a gaseous charge of predominantly carbon monoxide and hydrogen, but which need not have absolutely stoichiometric relationships corresponding to the above reaction equations, is fed to the plant via conduit 1. In the heat exchanger 2, the charge is heated to a temperature of about 250–300° C., which is sufficient to initiate the reaction in the first reactor stage 3 of a multistage reactor 4, to which the charge is fed via conduit 5, optionally after admixing steam from conduit 18.

A catalyst mass 6 is arranged within the first reactor stage 3. To prevent the methanization of the carbon oxide-containing charge gas from being completed in the first stage, the catalyst mass is designated, e.g. by dilution with an inert material or by the provision of a suitable catlayst mixture, so that the reaction velocity is sufficient for establishing the desired approach to the chemical equilibrium.

Moreover, at least one cooling coil 7, which carries cooling water, is arranged within the catalyst mass. Due to the evaporation of the cooling water, it is possible to remove at least part of the heat of reaction produced in reaction stage 3. As a consequence, the temperature of the gaseous mixture leaving the first reaction stage does not exceed a certain predetermined desired value, e.g. 480° to 500° C.

In case the temperature exceeds the intended desired value within the first reaction stage 3, for example due to faulty operation or carbon monoxide fluctuations in the charge or load variations, more water is vaporized within the cooling coil. In this instance, at least the thus-produced excess steam is admixed or introduced via nozzles directly into the charge gas to be treated, via a conduit 8 and a distributing device 31, whereby the temperatures within the reaction stage 3 are again lowered to the intended desired value.

The temperature reduction in the reactor effected by introducing the steam through nozzles into the gaseous charge occurs because of several factors. First, the addition of steam cools the gaseous charge. Second, an increased amount of gas must now be heated in the reaction stage 3, thereby diluting the exothermic heat. Third, due to the enlarged volume, a shorter residence time of the reactants in the catalyst chamber occurs (the mass flow rate of reactants being constant) resulting in a lower conversion rate. Last but not least, due to the steam which is fed thereto, the equilibrium of the reaction is shifted so that it is less favorable to methane formation, and the rate of reaction to methane formation is also reduced taking into account the inhibiting effect of the increased amount of steam on the kinetics of the reaction.

The gaseous charge is now passed at the desired temperature without intermediate cooling from the first reaction stage 3 into a further reaction stage 9 provided with a catalyst mass 10, a water cooling coil 11, and a steam feeding line 12, where the gas is subjected to the same treatment as in the first reactor stage 3.

The gas leaving the second reaction stage 9 is fed, again without intermediate cooling, to a last reaction stage 13 having a similar design as the two preceding stages, this last stage having a catalyst mass 14 and a water cooling coil 15. However, in this specific embodiment, no additional steam feeding line is installed in the last reaction stage, since it was found that the heat of reaction produced in the last reaction stage does not raise the temperature above the desired value of about 500° C. The amounts of catalyst in the individual reaction stages are dimensioned so that the gaseous charge is essentially in chemical equilibrium upon leaving the last reaction stage. This gas contains methane, hydrogen, carbon dioxide, water and minor amounts of carbon monoxide.

The water flowing in cooling coils 15, 11 and 7 is supplied by way of a central feed conduit 16 and withdrawn as steam from the plant via conduit 17. Optionally, part of the thus-produced steam can be fed directly via conduit 18 to the gaseous charge flowing to the reactor 4.

The feeding of the steam to reaction stages 3 and 9 via conduits 8 and 12 is controlled by means of valves 19 and 20, wherein the latter can be regulated, in turn, via suitable control mechanisms, for example by a conventional flow control valve (e.g. pheumatic or hydraulic) activated by signals from a temperature probe 22. Such automatic control systems are well known, attention being invited for example to Perry's Chemical Engineers' Handbook, 4th Edition, McGraw-Hill, Section 22.

The gaseous mixture leaving the last reaction stage 13 is withdrawn from the reactor 4 via lines 23 and cooled, in cooler 24, to the starting temperature of a supplemental reactor 26 provided with a catalyst mass 25. Within the reactor 26, at least a portion of the carbon oxides still contained in the gaseous mixture is methanized.

The gaseous mixture exiting from the reactor 26 and consisting essentially of methane, carbon dioxide, and steam, containing only minor amounts of hydrogen and carbon monoxide at this point, is cooled for purposes of an aftertreatment in the heat exchangers 2 and 27, and subjected to a water separation in the separator 28 and then to a carbon dioxide separation in the scrubbing column 29. A gaseous fraction is obtained in the head of the scrubbing column 29 comprising almost exclusively methane. This gas can further be utilized, for example, as synthetic natural gas. However, if still higher requirements as to methane purity must be met, the fraction obtained in the head of the scrubbing column 29 can optionally be subjected to a fine methanization step in a further reactor 30.

For further details of preferred embodiment of methane production, attention is invited to: "Hydrocarbon Processing", April 1974, page 69–74

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for conducting an exothermic chemical reaction comprising:
    (a) passing reactants into a reaction chamber zone, and within said reaction zone transferring exothermic heat of reaction indirectly to a liquid coolant in order to at least partially vaporize said liquid, and withdrawing resultant vaporized coolant from said reaction zone;
    (b) measuring the temperature inside said reaction zone, and comparing said temperature inside said reaction zone to a fixed maximum design temperature; and
    (c) when said temperature in said reaction zone intermittently exceeds said fixed maximum design temperature, surging at least a portion of said withdrawn resultant vapor from step (a) directly into said reaction zone to admix with the reactants and products in order to lower the temperature rapidly in said reaction zone to below the fixed maximum design temperature and
    wherein said chemical reaction is effected in several series-connected reaction zones, each zone being provided with a catalyst mass, wherein at least in the first reaction zone the catalyst mass is dimensioned so that the reaction velocity of the reactants is sufficient to produce a desired approach toward the equilibrium, but wherein not more than 95% equilibrium is attained, based on the theoretical quantity of product.

2. A process according to claim 1, wherein the chemical composition of the vaporized liquid corresponds to the chemical composition of a reaction product obtained during the chemical reaction.

3. A process according to claim 1, wherein the catalyst mass in the individual reaction zones is dimensioned so that the reactants are in substantial chemical equilibrium only after having passed through the last reaction stage.

4. A process according to claim 1, the chemical reaction being a methanization reaction, the reactants being a gaseous charge of carbon oxides and hydrogen, and wherein water is utilized as the liquid to be vaporized.

5. A process according to claim 4, wherein said fixed maximum design temperature is in the range of 480°–500° C.

6. A process according to claim 5, wherein the catalyst mass in the individual reaction zone is dimensioned so that the reactants are in substantial chemical equilibrium only after having passed through the last reaction stage.

7. A process according to claim 5, wherein vaporized water is passed in separate streams into the first two reaction zone in response to temperatures therein exceeding the maximum design temperature.

8. A process according to claim 5 wherein additional steam is continuously added to the reactants prior to entering the first reaction zone.

9. A process according to claim 1 wherein said surging of at lesst a portion of the withdrawn resultant vapor from step (a) directly into the reaction zone is discontinued when the temperature in the reaction zone is lowered to below the fixed maximum design temperature.

10. A process according to claim 8 wherein said surging of at least a portion of the withdrawn resultant vapor from step (a) directly into the reaction zone is discontinued when the temperature in the reaction zone is lowered to below the fixed maximum design temperature.

* * * * *

UNITED STATES PATENT AND TRADEMARK OFFICE
CERTIFICATE OF CORRECTION

PATENT NO. : 4,212,817
DATED : July 15, 1980
INVENTOR(S) : Herbert Schmid et al

It is certified that error appears in the above-identified patent and that said Letters Patent are hereby corrected as shown below:

Column 6, line 25: reads "lyst mass in the individual reaction zone is dimensioned"
should read -- lyst mass in the individual reaction zones is dimensioned --.

Column 6, line 31: reads "reaction zone in response to temperatures therein ex-"
should read -- reaction zones in response to temperatures therein ex- --.

Signed and Sealed this

Twenty-third Day of September 1980

[SEAL]

Attest:

SIDNEY A. DIAMOND

Attesting Officer

Commissioner of Patents and Trademarks